United States Patent [19]

Trabucco

[11] 4,378,023
[45] Mar. 29, 1983

[54] PERCUTANEOUS INSERTABLE ELECTRODE DEVICE FOR THE TRANSITORY OR PERMANENT STIMULATION OF THE HEART OR OTHER ORGANS AND A METHOD FOR IMPLANTING IT

[76] Inventor: Héctor O. Trabucco, Av.Sante Fe 2926,6°, 1425 Buenos Aires, Argentina

[21] Appl. No.: 154,583

[22] Filed: May 29, 1980

[51] Int. Cl.³ .............................................. A61N 1/04
[52] U.S. Cl. ................................. 128/785; 128/419 P
[58] Field of Search ............... 128/639, 642, 784, 785, 128/786, 419 P

[56] References Cited
U.S. PATENT DOCUMENTS

| | | | |
|---|---|---|---|
| 3,087,486 | 4/1963 | Kilpatrick | 128/642 |
| 3,568,660 | 3/1971 | Crites et al. | 128/419 P |
| 3,814,104 | 6/1974 | Irnich et al. | 128/419 P |
| 3,943,936 | 3/1976 | Rasor et al. | 128/419 P |
| 4,233,992 | 11/1980 | Bisping | 128/419 P |
| 4,280,503 | 7/1981 | Ackerman | 128/784 |

*Primary Examiner*—William E. Kamm
*Attorney, Agent, or Firm*—Fleit, Jacobson & Cohn

[57] ABSTRACT

A percutaneous insertable electrode device for transitory or permanent stimulation of the heart or other organs, comprising a rigid tubular member provided with perforating front means defining depth control means, a core removably housable in said tubular member, said core including projectable anchoring means and insulated electrical conductor means connected to said core and a method for implanting such electrode device.

23 Claims, 29 Drawing Figures

PERCUTANEOUS INSERTABLE ELECTRODE DEVICE FOR THE TRANSITORY OR PERMANENT STIMULATION OF THE HEART OR OTHER ORGANS AND A METHOD FOR IMPLANTING IT

BACKGROUND OF THE INVENTION

1. Field of the Invention

The present invention relates to a percutaneous insertable electrode device for transitory or permanent stimulation of the heart or other organs and to a method for implanting it.

Although the electrode device herewith proposed which is the subject of the present invention is primarily intended for heart stimulation, the possibility exists of implanting it in other organs, where under certain circumstances it may become necessary to provide stimulae through electric pulses. Reference is made to this concept, inasmuch as the electrode device of the present invention is based on a new concept which enables its implantation without major surgery, and is particularly useful for extreme emergency cases.

2. Description of the Prior Art

Before describing the invention, reference will be made to the different well known surgical approaches for implanting electrodes and the electrode types available.

(A) Pervenous implantation

Surgery, sometimes major surgery, is required to find an underskin vein having a suitable cross-section which enables the insertion therethrough of the electrode member. If a suitable underskin vein is not available, it is necessary to look for a deeper located and larger cross-sectional vein, which complicates the procedure itself. The spot where the tip of the electrode will have to be implanted in order to stimulate the inside wall (endocardium) of the heart, is in all cases at a distance of at least 45 cm from the surgical wound (point of insertion).

This way of stimulation has several additional difficulties apart from finding a suitable vein, one of which (as has been explained above) is the rather long distance through which the electrode member has to be inserted, and which implies a lack of precision to properly locate the tip of the electrode member to achieve a good electrical contact with the heart muscle. The lack of precision implies sometimes the risk of ventricular perforation.

Another drawback of this surgical approach is that sometimes it is necessary to look for another vein, due to the impossibility of reaching the right ventricle through the first chosen vein. This implies to withdraw the electrode member from the first vein and starting the insertion process again through another vein, in order to be able to anchor the electrode tip at a proper place.

A still further drawback of this surgical approach, is that when one has already unsuccessfully tried several veins, for instance cephalic, axillar or basilic veins, the main blood flow coming back from the arm, is stopped; this may imply later on, in the zone drained by those veins, functional upsetting, such as an arm edema.

Two rather important complications may furthermore happen with pervenous implantation:

(a) The interruption of stimulation due to dislocation of the electrode tip within the heart or, in the other words, impossibility of a permanent safe tip anchoring at a proper place once implanted in the right ventricle, and (b) Ventricular perforation with the consequent complication of a dangerous heart tamponate.

This surgical approach also involves an operation which is not suitable for emergencies, bearing in mind the time which is required to bring the patient to the X-ray room, as well as to prepare the instruments and the surgical team, who require the imperative use of a sophisticated X-ray equipment, to enable the main surgeon to watch the tip location within the heart, while performing the operation.

Once the tip has been located in the right hand chamber, fibrous tissue is developed surrounding the ventricular trabeculae, and such tissue usually anchors the tip in position, but if infection takes place, the system must be removed. If the electrode cannot be withdrawn, a well known terrible complication takes place, known as "trapped electrode" and it is necessary to open the heart with an extracorporeal circulation procedure, in order to withdraw the electrode. This is the most serious problem in connection with pervenous implantations.

If the patient suffers from a previous pathological condition (for instance Chagas-Mazza disease) right ventricle trabaculae are reduced and the anchoring of the tip of a pervenous electrode becomes impossible, since the inner wall of the right hand heart chamber is almost smooth.

B. Epicardic implantation

Two different surgical approaches are in use:

(a) A left hand thoracotomy (through left hand pleura) which implies a larger surgical risk, than that existing in the pervenous procedure (12% of morbidity in patients aged more than 50 years), bearing in mind that the cardiac pathology which is intended to be treated by cardiac stimulation, is usually carried out on patients aged more than 50 years.

(b) The second possibility includes other surgical approaches which avoid reaching the heart through the pleura. One of these is the subxiphoidous way, in which also major surgery is required.

In both cases the risk of ventricular wall laceration exists, and the resulting difficulty of sealing the wound, is outstanding. It should however be pointed out, that the size and shape of the ventricular wall laceration depends also on the device used to perform the stimulation.

The fact that the heart in both events becomes exposed, involves a considerable risk of infection. The electrode types available may produce additional risks of hurting other anatomical structures or organs in which stimulation is not necessary.

Another aspect which has to be borne in mind, is that certain pre-existing complications may be present on the myocardium (pericarditis). In this event no conventional (i.e. previously known) epicardic implantable electrode (due to their shape) can be used.

Since the epicardic approach is even more traumatic and therefore dangerous than the pervenous approach, both have to be discarded for emergencies.

Furthermore the obligatory use of X-ray equipment for the pervenous approach means that the surgeon and his team are always subject to such X-rays which obviously results in excessive radiation.

If the epicardic surgical procedure is used, although it does not require X-ray equipment, nevertheless it requires a larger surgical team which makes it still less suitable for emergencies.

C. Analysis of known electrodes to be pervenously and epicardically applied

Pervenous electrodes have been disclosed and used, having a corkscrew or curl-like tip portion to be screwed into the myocardium. This requires major surgery, as previously explained, with the difficult of finding a proper space. The possibility of ventricular perforation increases the surgical risks. Once the electrode member has been implanted, the withdrawal of the electrode member is extremely difficult. The curls of such tip have free pointed ends, so that the penetration into the heart muscle must be carried out by exerting pressure and rotation on the distal end of the conductor which defines the axis of the system. This type of electrode cannot be used in emergency cases. It is however true that such type of electrode decreases the tendency of movement of the anchored electrode tip in the right hand ventricle, but this arrangement increases however other types of risks, as pointed out above.

In certain cases, such as pacemaker migration or due to involuntary movements while performing surgery, a certain pull may be exerted on the electrode, which can produce serious complications, such as laceration and perforation of the ventricular wall.

Other epicardic electrodes offer not only the above mentioned risk of thoracotomy, but it is necessary to insert stitches, in order to properly anchor such electrodes to the heart. It is also necessary to expose a large surface of the heart with the evident drawback that large anathomic structures have to be surgically exposed. If it should become necessary to withdraw the electrode, this may involve a permanent perforation remaining in the heart, upon withdrawing the helically shaped tip, which can have fatal consequences. An accidental tension exerted on the electrode or a movement of the pacemaker after the electrode having been anchored, implies further risks. In addition, other complications may happen while performing the implantations due to the difficulties of finding a free fatty area on the epicardium. It is well known that fatty tissues do not allow the surgeon to perform a safe anchoring in it, so that when anchoring has to be carried out through a fatty tissue, and by using a corkscrew type or helicoidal tip, more pressure and a more pronounced rotation must be exerted in order to achieve a reasonable safe anchorage in the heart muscle. This procedure produces, particularly in weak muscles, laceration of the heart muscle with the obvious risks.

To withdraw such an electrode, because of infection (more than 3% develope infection) or other reasons, becomes extremely difficult, because a new operation is necessary, and the tip has to be unscrewed from the heart muscle. If a pin tip with a a stitched on base member is used, the stitches have to be cut, all of which is extremely difficult due to the fibrous tissue growth at the respective portions after the first operation, as already explained.

A third type of electrode known as Irnich-Rosenbauer has been described for pervenous implantations and which comprises two hooks projecting from inside a flexible cylinder member and which are to be anchored in the muscular wall. This electrode has been used for atrial stimulation. It cannot be used percutaneously because of its large cross-section. Such electrode needs an outer flexible guiding cylinder and the patient must have extremely large cross-sectional veins. Its fixing is extremely difficult due to:

(a) ist length,
(b) the long stylet required to project the hooks out of the flexible cylinder, and
(c) the sinous path defined by the organs to reach the proper place;
(d) the use of such electrode requires an X-ray equipment.

Moreover, for anchoring this device, a certain pressure has to be exerted on its tip to eject the hooks to anchor them and thereby the electrode. Once such electrode has been anchored, it is necessary to link it to some portion of the vein to avoid the natural reaction of the heart to expel any press-fitted element within it. The orientation of these hooks of the electrode tend to move the electrode easily. It should be borne in mind that the arrangement of these hooks is such that the axis of each hook, in operative position, defines an inclined plane with regard to the axis of the core of the electrode, taking as a reference the distal end thereof. Thus, if there were not some way of further anchoring of the electrode, which maintains the latter constantly against the cardiac muscle, its use would certainly increase the danger of tip dislocation. Furthermore, in view of the shape of its hooks, it is necessary to apply pressure on the distal end of the electrode in order that the hooks become properly anchored; this also increases the risk of perforation of the chamber. In addition, to what has been just stated, obviously major surgery is necessary in these cases.

SUMMARY OF THE INVENTION

Bearing in mind the difficulties concerning the insertion and anchorage of all known types of electrodes, a new concept has been seeked, whereby:

(a) It should not be necessary to carry out extensive preparations for anchoring the electrode, i.e.: of instruments, surgeons and their assistants and it should become possible to insert the electrode without requiring specialised surgeons.

(b) The simplicity of inserting the electrode should be such that even a physician who is not a surgeon, should be able to perform the task in emergency cases.

(c) The patient should not be exposed to large surgical traumatism upon using the epicardic access, because the electrode should be anchorable through a mere percutaneous punction.

In general, the electrode of the present invention is a percutaneous insertable electrode device for the transitory or permanent stimulation of the heart or other organs, comprising a substantially rigid tubular member having a front end forming a first diameter, a needle-like tubular member having a second diameter smaller than said first diameter (and being sufficiently small to allow perforating the endocardium of the heart without creating harm upon withdrawing it), said needle-like tubular member defining a forward end which projects beyond said front end of the tubular guide member by a distance which is approximately equal to half of the mean average thickness of the myocardium of the heart muscle, a core removably housable in said tubular member, said core including projectable and retractable anchoring means and insulated electricity conductor means connected to said core.

In one of the embodiments according to the present invention, the percutaneous insertable electrode device for the transitory or permanent stimulation of the heart and other organs comprises a core having a front portion and a rear portion, at least one resilient anchoring member having a first pointed free end and a second end which is linked to said core and which has, a substantially complementary housing, for said anchoring member, said first pointed free end of said anchoring member having a tendency to project out of its housing, said anchoring member being capable of adopting an inoperative position in which it is substantially housed in said substantially complementary housing, and an operative position in which said anchoring member projects out of said housing with an orientation defining as a maximum an approximately right angle with regard to the axis of the core taking as a reference the rear portion of the core, an electrical conductor connected to at least one of said core and anchoring member, said conductor being arranged in an insulated sheath connected to the rear portion of the core and a hollow substantially rigid tubular guide member having a front end portion defining a perforating mouth and which is slideably mounted on said core and projects beyond the rear portion of said core said perforating mouth is controlled by depth control means.

In another embodiment, according to the present invention, the percutaneous insertable electrode device for the transitory or permanent stimulation of the heart or other organs, comprises a substantially rigid tubular guide member having a front end; a needle member having a forward end portion, said needle member being longer than said guide member and having an overall cross-section smaller than the internal cross-section of said tubular guide member, said needle member being slideable through said guide member, said needle member including an enlarged sealing portion near said forward end portion adapted to enter in sealing contact with the inside of said front end; an electrode tip including a core pivotally supporting at least one U-shaped anchoring needle formed by a curved front prong, a curved rear prong and a connecting base portion, said connecting base portion being journalled in said core, recessed portions in said core for housing said prongs therein, said core with the prongs housed in their recesses having an overall cross-section smaller than the internal cross-section of said tubular guide member, said prongs being projectable out of said core upon rotating said electrode tip in one direction and being rotatable into said recessed portion upon rotating said electrode in opposite direction to said first direction, an insulated electricity conductor electrically flexible connected at least to one of said core and anchoring needle capable of passing, together with said tip through said guide member, and a dismountable stylet connectable to said core for moving said core forward as well as for rotating it.

Furthermore, the present invention relates to a method for implanting from outside of the patient's body an electrode device in an internal organ, such as the heart (without requiring thoracotomy or the like procedure to gain previous access to the internal organ to be stimulated by electric pulses), comprising the steps of perforating the patient's skin with a tubular hollow, substantially rigid guide member including at its forward end a forwardly projecting perforating needle, moving said guide member forward towards the organ where the electrode is to be implanted, partially penetrating in said organ from outside with said needle and the forward end of said guide member, detecting the depth of penetration through said needle, passing through said guide member an electrode tip having projectable and retractable anchoring means at least in the front portion of said tip, the rear portion of which is connected to a flexible insulated electricity conductor, moving said electrode tip forward until said front portion of said tip is substantially flush with the forward end of said guide member, withdrawing the guide member along said electrode tip and insulated electricity conductor out of the patient's body at the same time as the projectable anchoring means are anchored in the internal organ.

The hereinabove defined electrode members offer the following advantages:

The fact that the heart muscle need not be exposed, provides a less possibility of infection.

The fact that no X-ray equipment is required, enables the electrode member to be anchored under any circumstances, even if the patient is in his bedroom or laying in the street.

The electrode member provides a simple solution (due to the means used) for searching and finding a suitable point for inserting the electrode member, to achieve a satisfactory cardiac stimulation.

The point of insertion can be changed easily in view of the simple way by which an anchored electrode member according to the present invention can be removed and which will be described in a more specific way in connection with several of the embodiments shown in the accompanying drawings and to which references will be made later on.

If the removal of the electrode member may become necessary for any of the above referred to reasons it does not imply any complication, because upon anchoring such an electrode member in the heart muscles one is sure that the inner heart wall has not become perforated, thus the anchorage may have taken place either only in the epicardium or in the epicardium and part of the outer zone of the myocardium.

Furthermore any accidental tension exerted on the electrode member or due to pacemaker migration, will not involve any laceration, of substantial consequences of the inner cardiac muscle (endocardium).

The use of the electrode member according to the present invention, once correctly inserted, assures that the anchorage takes place in the muscular mass (myocardium) without reaching the endocardium and therefore a good contact between the muscle and the tip of the electrode is achieved in order to stimulate the heart muscle with the proper intensity.

The percutaneous insertion does not require well trained people, such as specialized surgeons, since it is not necessary to carry out any major surgery.

The simplicity of the method of inserting the electrode member enables the insertion of one or more electrode members due to the samll electrode size. The use of several electrodes at a time is almost impossible with any of the known procedures and conventional electrode members.

The anchorage of the electrode member, according to the present invention, is carried out by a device having means which resist any action of the heart to expel the anchorage, whereby an excellent safety coefficient is achieved at the same time as an easy removal of such electrode member is likewise possible. The combination of these conditions or at least part of them has never been achieved prior to the present invention.

The Stokes Adams crisis (fainting, low pulse of 40 or less beats per minute) which causes poor brain irrigation, so frequent in this type of patients, where it is a fundamental requirement to connect a pacemaker, produces in many cases a substantial unforeseeable traumatism or sudden death, due to cardiac arrest or ventricular fibrilation. It is known that the restablishment of the normal cardiac frequency by means of electric stimulation is the most successful known method for saving life. It is in this case where a most outstanding advantage is provided by the electrode device of the present invention, inasmuch as it does not require the preparation of a whole team of surgeons and the electrode device can be anchored within three to five minutes operation, thereby protecting the brain from any irreversible damage. The simple epicardic punction which is to be performed with the electrode according to the present invention enables the above outlined difficulties to be overcome, since the brain can only survive without damage for a very short period. The electrode device according to the present invention is therefore a new device which can be anchored within an extremely short time, so that it fills out a blank within medicine, which up to now was an unsolved problem.

BRIEF DESCRIPTION OF THE DRAWINGS

In order to explain the structural principles of the electrode devices according to the present invention, reference will now be made to the appendant drawings, in which several embodiments are disclosed, which facilitate the comprehension of the principle of the invention, more particularly.

DETAILED DESCRIPTION OF PREFERRED EMBODIMENTS OF THE INVENTION

Figure 1:
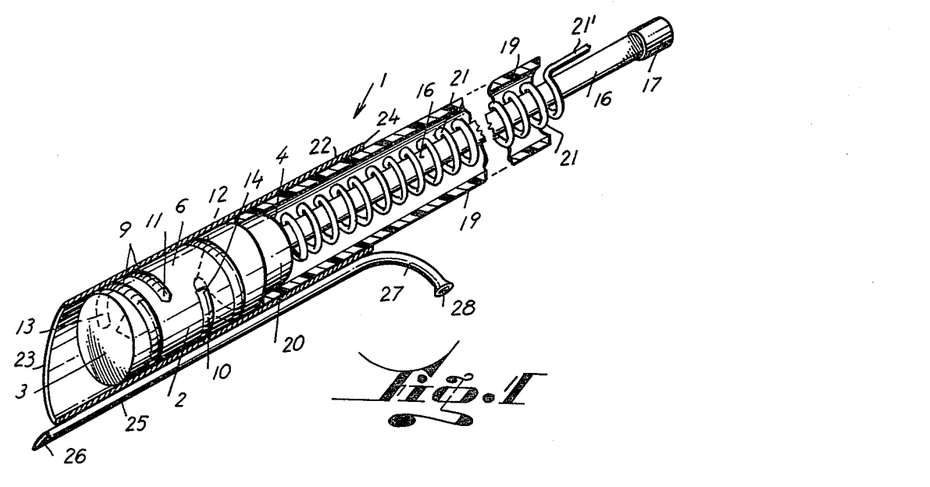
FIG. 1 is a perspective view, partially in section, of a first embodiment of the electrode device of the present invention, shown prior to implantation.
Figure 2:
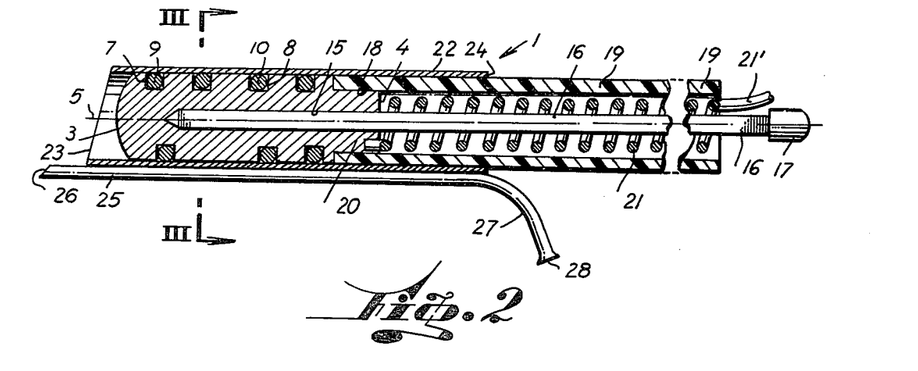
FIG. 2 is a longitudinal section of the same electrode device.
Figure 3:
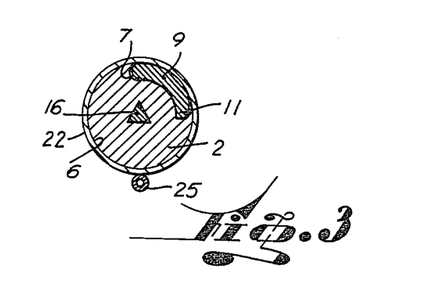
FIG. 3 is a cross-section along line III—III of FIG. 2.

Referring now to FIGS. 1 to 3, the electrode device 1 of the present invention comprises a core 2 which in this embodiment is made of a good electrically conducting material and which defines a front face 3 and a rear face 4. The core 2 is of cylindrical shape and the rear face 4 is inclined, with regard to the longitudinal axis 5 at a right angle. The cylindrical periphery 6 of the core 2 has two channel-like recesses 7, 8 which each define a helical curl or turn and which are spaced apart from one another. In the embodiment shown the channel-like recess 7 is located nearer the front face 3 than the channel-like recess 8. In each of said recesses 7, 8 a respective resilient anchoring member 9, 10 is arranged, having a first pointed free end 11, 12 and a second end 13, 14 which is connected to the core 2. The second ends 13, 14 are arranged nearer the front face 3 than the first ends 11, 12. The core 2 has a blind bore 15, coaxial with axis 5, which ends in the rear face 4 and which has a triangular cross-section.

An operating stylet 16 is fitted into the blind bore 15 and projects from the rear portion of the core 2 ending in an operating knob 17. The blind bore 15 and the stylet 16 are coaxial with the axis 5. The stylet 16 may be withdrawn from the core 2.

The rear end of core 2 has a shoulder 18 on which a resilient sleeve 19 of electrically insulating material is filled and the thickness of which is such that it is preferably flush with the cylindrical periphery 6. The rear portion 20 of the core 2 is connected to a helical electrical conductor 21 which projects from the rear portion of the sleeve 19, as indicated by reference numeral 21'; this rear end 21' is to be connected to an electric pulse generator source and which is normally a pacemaker (not shown).

The channel-like recesses 7 and 8 have a substantially complementary shape with regard to the anchoring members 9 and 10, so that these members may be substantially totally housed within said recesses 7, 8, in order that the cylindrical core member 2 maintains its shape through its length with the anchoring members 9 and 10 housed therein.

A tubular hollow, rigid guide member 22, which has a front end 23 which defines a perforating tip, is slideably mounted on said core 2 and projects at its rear end 24 beyond said core 2 when the front end 23 is located beyond the front face 3 of the core 2. The length of said guide member 22 must be long enough to reach the heart from the skin, and shorter than the length of the portion of the electrode member 21, 19 remaining outside of the body. Along the lower portion of said tubular guide member 22, a needle-like tubular member 25 is located, the forward end 26 of which is a perforating end and which projects beyond the front end 23 of said tubular guide member 22 by a distance which is approximately equal to half of the mean-average thickness of the myocardium of the heart muscle. Conveniently the rear end portion 27 of the needle-like tubular member 25 projects from the rear end portion 24 of the tubular guide member 22, defining an arcuate portion which ends into a funnel 28.

The steps which have to be carried out with this electrode device in order to anchor the core thereof in the heart muscle will now be described with reference to FIGS. 4 to 8. In all these Figures the skin of the patient is shown schematically and identified by reference numeral 29 which is followed by an adipose layer 30 spaced apart from the eipcardium 31 of the heart by an intermediate zone 32. The heart 33 is schematically shown as further comprising a myocardium 34 and an endocardium 35. It is known that the muscle which defines the heart 33 is pain in sensitive, while this is not true of the zones 29, 30 and 32, as above defined.

Figure 4:
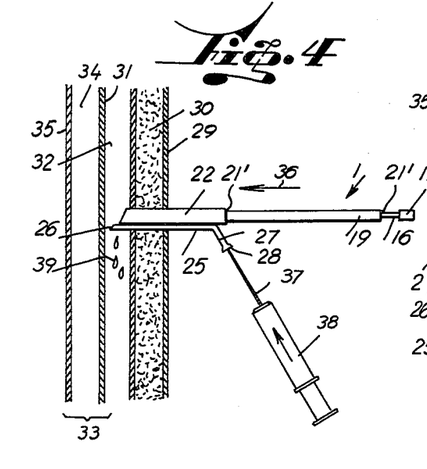
FIGS. 4 to 8 show successive steps for implanting the electrode device of the first embodiment and anchoring it in the heart.
Figure 5:
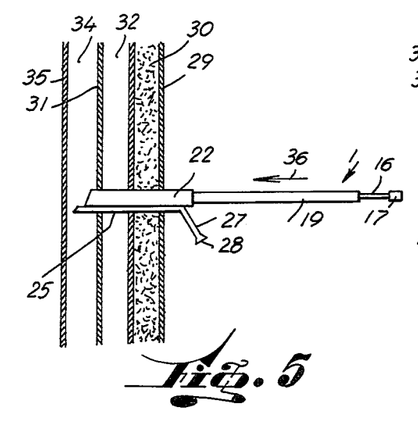
Figure 6:
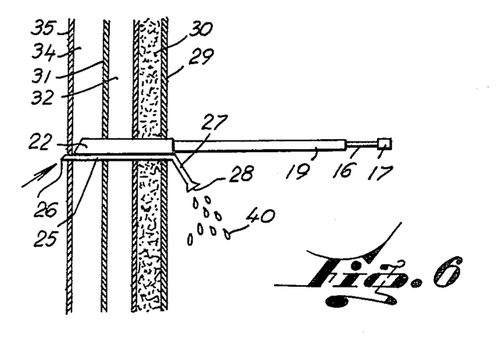

In order to insert and anchor the electrode device 1 of the present invention in the heart 33, the surgeon starts to perforate the skin 29 by moving the electrode device 1 in the direction indicated by arrow 36. At the same time the needle 37 of a syringe 38 is inserted into the funnel 28 and an anaesthetic is started to be injected, which anaesthetic may eventually be mixed with other drugs (in unconcious patients following a cardiac arrest it will be the fastest way to inject drugs to help heart reamimation, since anaesthetic drugs are not necessary) and which will be ejected, as schematically shown by means of drops 39, whereby the electrode device can be moved forward towards the epicardium 31 without any substantial pain. At the moment the front tip 26 of the needle-like member 25 enters the heart 33, the electrode device will start to oscillate due to the transmission of the heart beats. At this moment the surgeon will become aware that he has reached the heart 33 without it being necessary to have an X-ray equipment and this is also the indication for the surgeon, as shown in FIG. 5 to withdraw the syringe 38 from the funnel 28, since no more anaesthetic drug is required. The insertion of the electrode device, is continued by moving the electrode member forward in the direction indicated by arrow 36 until, as shown in FIG. 6, the front end 26 of the needle-like member 25 perforates the endocardium 35 at which instant blood will enter the front end 26 and become discharged through the funnel 28, where such blood is illustrated by means of the drops 40. In this position the forward end 23 of the tubular hollow, rigid guide member 22, which also carries out a perforating action, has not yet reached the endocardium 35. In other words when blood flows out through the funnel 28 of the needle-like member 25, the surgeon knows that he has to stop the forward movement, and that at this instant the hollow tubular guide member 22 is still within the myocardium 34 and proper room has been achieved for the core 2. It should be added that the rigid guide member 22 need not be manufactured of metal, it can be made for instance of a suitable plastic, such as polytetrafluorethylene available under the Trade Mark "Teflon", to have a certain flexibility, provided that the inside diameter always remains substantially constant.

Figure 7:
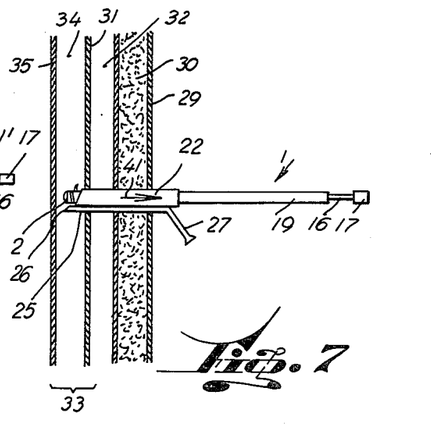

At this instant the actual anchoring steps will start, to which end, as shown in FIG. 7 the surgeon starts to withdraw, in the direction indicated by arrow 41, the tubular hollow, rigid guide member 22 together with the needle-like member 25, whereby the discharge of blood stops as soon as the forward end 26 enters again enters the myocardium. During this step the surgeon will with one hand maintain the core 2 in its inserted position, to which end he holds the core in its position by means of the knob 17 and thereby also the resilient sleeve 19, while the other hand moves the assembly of the tubular guide member 22 and needle-like member 25 in a direction to withdraw it from the patient, to reach finally the position shown in FIG. 8. Once the tubular guide member 22, together with the needle-like member 25 has been withdrawn from the core 2, the free pointed ends 11, 12 of the anchoring members 9, 10 due to their own resilience, start to project out of the cylindrical periphery 6 of the core 2 and the surgeon starts now to rotate the knob 17 in the direction indicated by arrow 42 or in other words, to unwind the turns 9, 10 from the core 2 and make them enter the myocardium 34 through their pointed ends 11, 12, respectively, whereby the core 2 becomes anchored in the myocardium 34.

Conveniently the pointed ends 11, 12 are staggered by 180° when being mounted in their respective channel-like recesses 7, 8, as can be best seen in FIG. 1.

Figure 8:
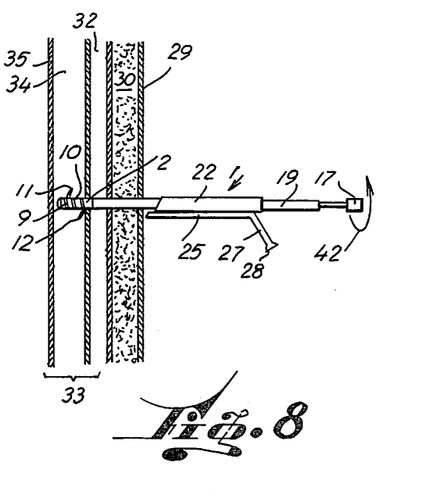

Once the electrode 1 has been anchored in the heart, the tubular guide member 22 together with the needle-like member 25 can be easily withdrawn and also the stylet 16 is withdrawn from the blind bore 15 and from the resilient sleeve 19.

In case of an extreme emergency, the rear end 21' of the electrical conductor 21 can now be connected to the electrical pulse generator. If there is no such urgency, it is possible to continue with the operation by reinserting the resilient sleeve 19 with its conductor 21 underneath the skin 29 in order to lead the rear end towards the anatomic "pocket" where the pacemaker (not shown) is to be implanted and to connect the rear end 21' to such a pacemaker. Since said latter step (connecting step) is a known operative procedure, further details are not necessary.

As will be readily apparent, it is possible, instead of providing a single electrical conductor to be connected to the rear portion 20 of the core 2, that an electrical conductor could be used in combination with a non-conducting core member and that the conductor could be connected to the two anchoring members 9 and 10 or two conductors could be provided connected to respective anchoring members if a bi-polar electrical circuit is desired. It is also evident that the core of the electrode device could operate successfully if only one anchoring member were provided.

In the example described, the anchoring members define, when open, an angle which is approximately a right angle with regard to the axis 5 of the core 2, taking as a reference the rear portion 20.

As already explained, the insertion of the anchoring members into the myocardium is achieved by rotating the core 2 about its longitudinal axis 5; if the core is to be withdrawn, such as for instance in the event of an infection or if a reinsertion is to be made at another portion of the heart, it is sufficient to proceed in an opposite sequence of the steps previously described. Obviously, upon reinserting the operating stylet 16 and rotating the latter in a direction opposite to that indicated by arrow 42 in FIG. 8, the anchoring members become again housed in the core, whereby it becomes possible to reinsert the hollow rigid tubular guide member 22 and then to withdraw the electrode device without any substantial laceration taking place in the heart muscle.

It is to be added that the needle-like member 25 does not only allow the location of the core in a proper position within the myocardium, but it also enables the simultaneous provision, apart from anaesthetic, of any drug which contributes the restablishment of the cardiac function in case of extreme emergency. The practice of injecting drugs directly into the heart is well known, since in the case of cardiac arrest or of an extreme arrythmia there is no peripherical circulation and the pharmaceutical action on the heart is only possible by a direct injection. There is no prior system which operates on the combined basis, that is to say to provide electric stimulation to the heart and to co-operate simultaneously therewith by means of drugs. It should furthermore be borne in mind that by means of the same needle-like tubular member it is possible to simultaneously compensate any other type of desequilibrium always present in extreme emergencies, such as pronounced metabolic acidosis. Finally, it is to be pointed out that the use of the needle-like tubular member becomes extremely important when no accessible veins are available or not easy to find or when no pervenous electrodes are available or when there is excessive fat tissue.

The principle of the present invention is not limited to the requirement of having to turn the core in order to carry out its anchoring.

To this end two further embodiments will now be described which show that the anchoring may be carried out likewise by moving the core lengthwise in the direction of withdrawal from the heart.

Figures 9, 10, 11:
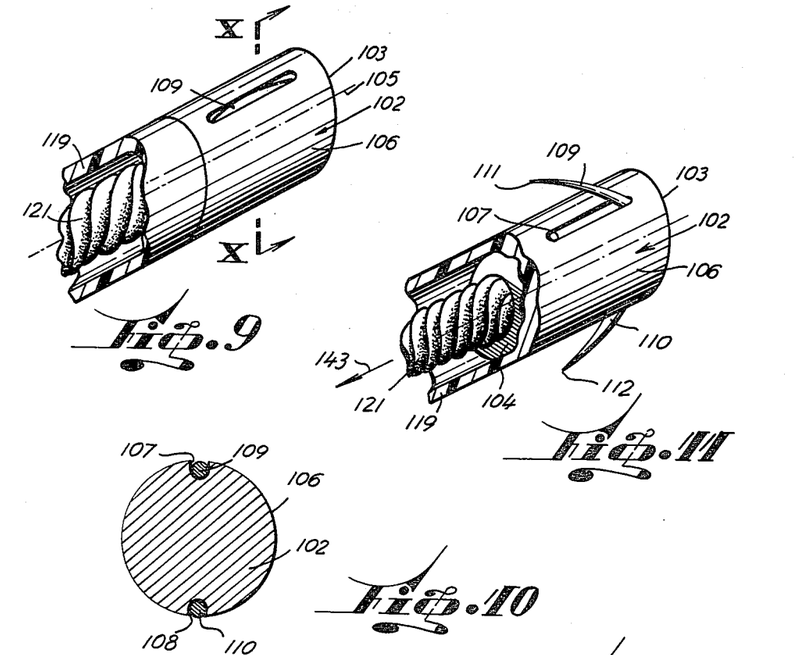
FIG. 9 is a perspective view of a second embodiment of the core of an electrode member with its anchoring members in inoperative position, an electrical conductor and an insulating sleeve, the last partially in section.
FIG. 10 is a cross-section along line X—X of FIG. 9.
FIG. 11 is a perspective view, similar to FIG. 9, but showing the anchoring members in operative position.

Referring now to FIGS. 9 to 11, where the same reference numerals have been used to indicate similar members, but which are preceded by the prefix "100", it may be appreciated that the core 102 is connected by its rear face 104 to an electricity conductor 121 which is a braided conductor, so that tension may be exerted thereon in the direction indicated by arrow 143 in FIG. 11. The core 102 has two diametrically opposed channel-like recesses 107 and 108 which in this example are parallel to the axis 105 and are capable of housing respective anchoring members 109, 110 having pointed end portions 111 and 112 which are directed towards the rear face 104 and the opposite ends of which are connected to the respective portions of the recesses 107 and 108, respectively, in the core 102. Each resilient anchoring member has a tendency to project out of the periphery 106 by means of its pointed end portions 111 and 112, as soon as the tubular guide member is withdrawn therefrom. This has not been shown in these Figures but is similar to the one described in FIG. 1 and identified there by reference numeral 22. Conveniently, the sleeve 119 is somewhat more rigid than the sleeve 19, in order to be able to push the electrode device to carry out the steps described in relation to FIGS. 4 to 6. As soon as the electrode device reaches the step corresponding to FIG. 7, the latter is carried out by pulling on the electrical conductor 121, which is tension resistant and which to this end is of the braided type, as well as on the sleeve 119.

It will be understood that upon withdrawing the hollow, rigid tubular guide member, not shown, the pointed ends 112 and 111 start to emerge out of the periphery 106 of the core 102 and upon exerting a tension in the direction of arrow 143 the anchoring members 109, 110 will penetrate into the myocardium. This embodiment shows that it is not necessary to rotate the core 2 about its axis 105 in order to anchor said core.

In this embodiment it is not possible to withdraw the the electrode again, if required.

Figure 12:
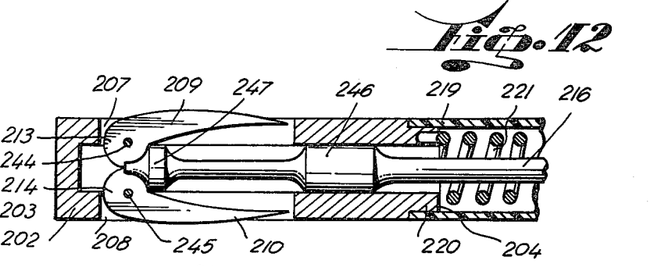
FIG. 12 is a longitudinal cross-section of a third embodiment of the core of an electrode with its anchoring members in inoperative position, an electrical conductor member and an insulating sleeve, the last partially in section.
Figure 13:
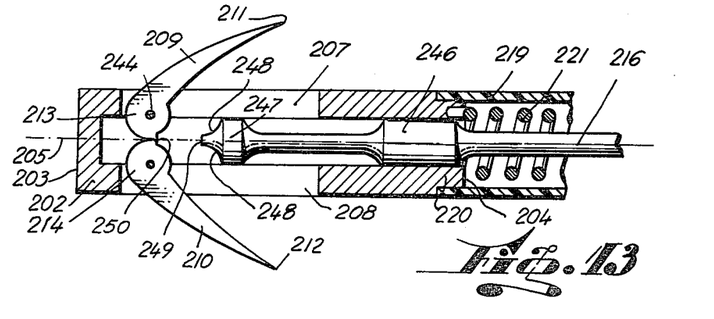
FIG. 13 is a longitudinal section, similar to FIG. 12, but showing the anchoring members in operative position.

An embodiment which is able to carry out withdrawal using the same structural principle as that of the second embodiment, shown in FIG. 12 and 13, in which the same reference numerals are used for similar parts as for the first embodiment, but which are preceded by the prefix "200".

In this embodiment the core 202 is a hollow member having a pair of diametrically opposite slots 207 and 208 which are the equivalent of the channel-like recesses 7 and 8 of the first embodiment and through which respective anchoring members 209 and 210 may project which likewise have free pointed end portions 211, 212, but the rear portion of each defines a pertinent cam 213, 214 rigidly mounted on torsion shafts 244, 245 which tend to project the pointed end portions 211 and 212 out of the slots 207, 208 as shown in FIG. 13, once the hollow tubular guide member (not shown in this embodiment) is withdrawn. Accordingly, the insertion of the anchoring members 209, 210 into the myocardium layer of the heart is carried out in the same way as described in connection with the embodiment of FIGS. 9 to 11 by carrying out a pulling action only on the sleeve, which has the necessary strength to resist the tensional force used. If the anchoring members 209, 210 have to be reinserted into the core 202, then a special stylet 216 is used having an intermediate portion 246, the cross-section of which is equal to the internal cross-section of the hollow core 202, which acts as a guiding member in order to be able to move said stylet 206 coaxially along the longitudinal axis 205 and the conductor 221. The forward end 247 of stylet 216 ends in an hyperbolic portion 248 having a blunt point capable of pushing on the shoulders 250 of the cams 213, 214. Upon moving stylet 216 towards the front face 203 of the core 202, it is possible to reinsert the anchoring members 209, 210 into the slots 207, 208. While such step is carriet out, obviously the core has to be moved forward towards the endocardium.

It also follows from the foregoing that the hollow rigid tubular guide member 22 has not necessarily to be provided with the needle-like tubular member 25, since it is possible to carry out the anaesthetic injection through an independent syringe, although in such event there is no straight forward control of the position of the core member, depending then on the capacity of the surgeon to know up to where he can move the core member into the heart muscle.

A fourth embodiment will now be described with reference to FIGS. 14 to 29, in which the same reference numerals are agains used for similar parts as for the first embodiment, but which are preceded by the prefix "300".

The fourth embodiment differs from the first embodiment in respect of the needle-like tubular member 25. In the first embodiment the tubular hollow, substantially rigid guide member 22 forms a rigid unit with the needle-like tubular member 25, which is integrally located on the outside of said tubular guide member 22, whereby the overall cross-section is rather large and in certain cases the advancing of the electrode device 1 from the skin towards the heart may become difficult. In the fourth embodiment the needle-like tubular member 325 is removable, and may be inserted through the guide member 322 and withdrawn therefrom, once the combination of the members 325 and 322 has been inserted in the heart as shown in FIG. 6, in connection with the first embodiment. After this the electrode member 302 is then inserted through the guide member 322, which remains stationary in the position inserted in the heart, as will be explained. Likewise in this embodiment the guide member 322 may be made of plastic.

Figures 14, 15, 16, 17, 18:
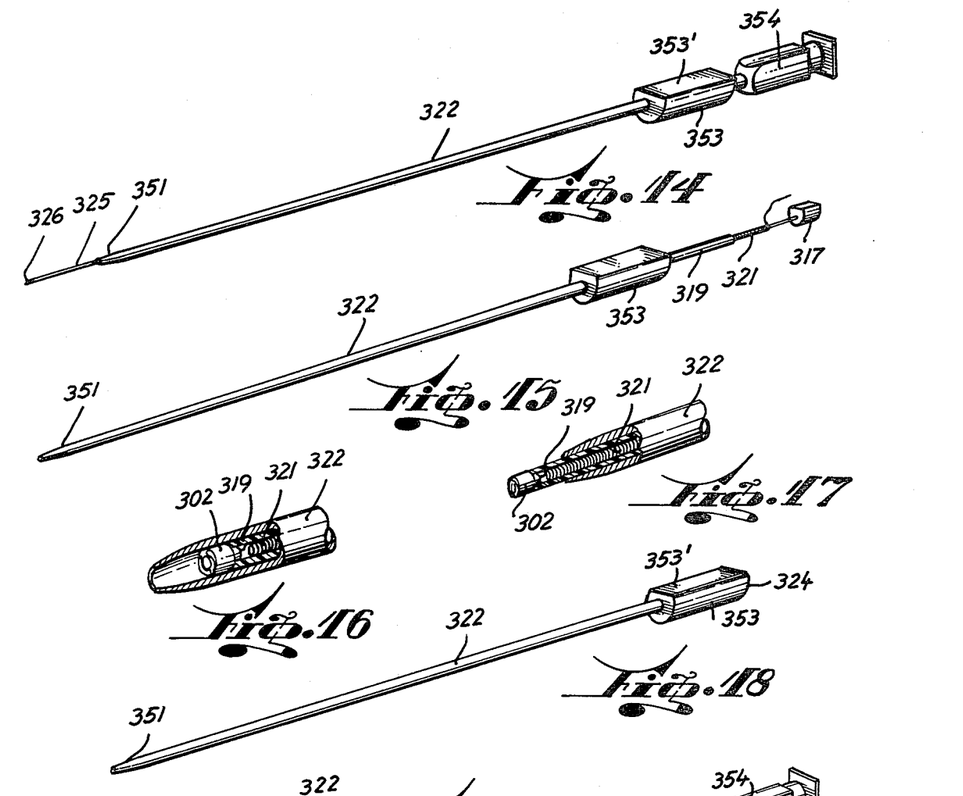
FIG. 14 is a perspective view of the assembly of a rigid tubular guide member and a needle member forming part of a fourth embodiment of a percutaneous insertable electrode device in accordance with the present invention.
FIG. 15 is a perspective view of an assembly of a rigid tubular guide member shown in FIG. 14, but now in combination with an electrode member.
FIG. 16 is a detail in perspective view and partially in cross-section, of the forward end portion of the rigid tubular guide member, to show its tapered mouth and part of the electrode member before having reached said tapered mouth.
FIG. 17 is a detail in perspective view and partially in cross-section, similar to FIG. 16, but showing the electrode member after having passed through the tapered mouth.
FIG. 18 is a perspective view of the rigid tubular guide member.
Figures 19, 20, 21:
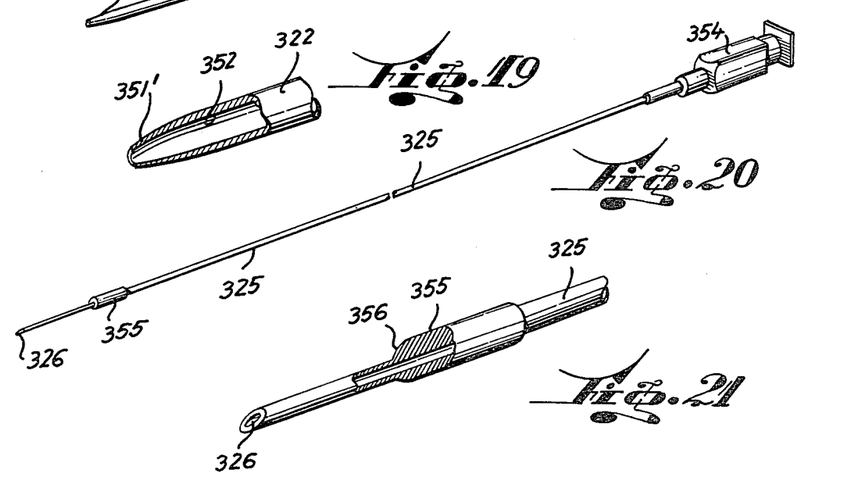
FIG. 19 is a detail in perspective view and partially in cross-section, of the forward end portion of the rigid tubular guide member.
FIG. 20 is a perspective view of a needle member.
FIG. 21 is a detail in perspective view, partially in section of the front end of the needle member.

Referring first to FIGS. 18 and 19, the guide member 322 consists of a tubular, hollow substantially rigid member, having a front end which defines a tapered mouth 351, where the wall member 351' decreases in thickness towards its mouth, so that the actual front end thereof is somewhat resilient. The bore 352 has a constant diameter throughout the entire length of the guide member 322 with the exception of the tapered mouth 351, where the wall member 351' slightly decreases in thickness. The rear end portion of the guide member 322 ends in an abertured operating handle 353, having a flat portion 353', which facilitates the handling of the guide member 322. Thus, the operating handle 353 defines a rear end portion 324 which is equivalent to the rear end portion 24 in the first embodiment. The length of the guide member 322 has to be larger than the distance existing between the skin and the organ of the patient, which is to be implanted with the electrode member, so that the operating handle 353 will always remain outside of the patient's skin (not shown).

Referring now to FIGS. 20 and 21, an independent needle member 325 is there shown, having a sharpened sloped forward end 326 and a rear head 354, which is the equivalent of the funnel 28 in the first embodiment and through which a syringe 38 (see FIG. 4) may be inserted. The total length of the needle member (previously referred to as the needle-like tubular member) 325 is greater than the total length of the tubular guide member 322. The needle member 325 comprises an enlarged sealing portion 355 having a frusto-conical front portion 356, which may enter in sealing contact with the wall member 351' of the tapered mouth 351 whereby, as shown in FIG. 14, the front portion of the needle member 325 with its sharpened tip 326 projects out of the guide member 322 by a distance equivalent to the front portion of needle member 25 with regard to the front end 23 of the guide member 22, as described in connection with the first embodiment (see FIGS. 1 and 2), so that the combination of the guide member 322 and the needle member 325, when assembled as shown in FIG. 14 can be used to carry out the steps as explained in connection with FIGS. 4 to 6 in relation to the first embodiment. The frusto-conical front portion 356 has to provide the necessary sealing, to ensure that no blood will be capable of entering into the guide member 322 between the needle member 325 and the bore 352 (see FIGS. 19 and 21). Once this device has been inserted in the heart to reach the step as described in connection with FIG. 6, the surgeon will withdraw the needle member 325 from the guide member 322, which is maintained in its position, and then insert into the guide member 322 the electrode member of the fourth embodiment, the structural details of which will now be described, in connection with FIGS. 22 to 29.

Figure 22:
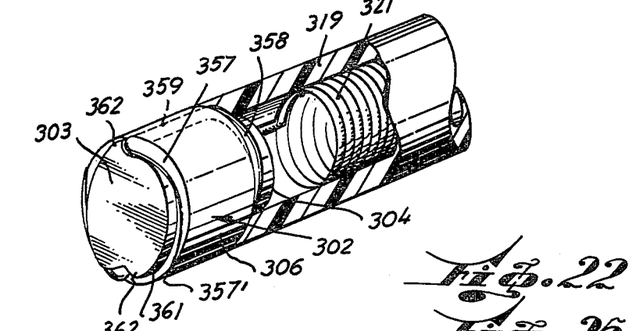
FIG. 22 is a perspective view, partially in cross-section of the front end of the electrode member in the fourth embodiment.
Figures 27, 28, 29:
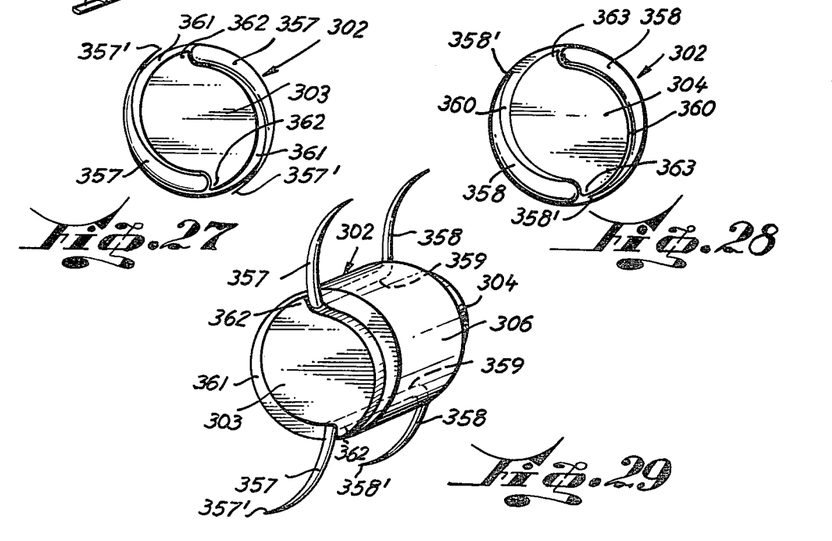
FIG. 27 is a front end view of the electrode tip with front prongs housed in respective recesses.
FIG. 28 is a rear end view of the electrode tip with rear prongs housed in respective recesses.
FIG. 29 is a perspective view of the electrode tip, showing the front end rear prongs in open or operative position and the stops provided by the electrode tip to limit the emerging path of the U-shaped anchoring needles with regard to the core.

The actual electrode member consists in this embodiment of a cylindrical core 302 which has a front face 303 and a rear face 304. The front end portion as well as the rear end portion are each recessed in order to house therein respective anchoring members. More particularly, in this embodiment two anchoring members are provided each consisting of a U-shaped anchoring needle, formed of a curved front prong 357 and a curved rear prong 358, linked together by means of an integral connecting base portion 359. The connecting base portion 359 of each U-shaped anchoring needle is journalled in a respective bore coaxial with the longitudinal axis of the core 302 and which allows the prongs 357 and 358 to oscillate between a collapsed position, as shown in FIGS. 22, 27 and 28 and an operative or projecting position, as shown in FIG. 29. All of the prongs 357, 358 end in a point, but the curve of each front prong 357 is slightly more open than the curve of each rear prong 358, so that when the U-shaped anchoring needles are in collapsed position, the pointed ends 357' (FIG. 27) project slightly beyond the periphery 306 (FIG. 29) of the core 302, while the pointed ends 358' of the rear prongs 358 (FIG. 28) will remain housed within the respective recesses 360. The front end portion defines the recesses 361 as best shown in FIG. 22 and each recess 360 and 361 forms adjacent the connecting base portion 359, a projecting stop 362, 363, which ensure that the prongs 357, 358 may not open beyond a predetermined point in the path from the collapsed position towards the open position.

As in the first embodiment, there is an electrical conductor 321, which is housed in an insulating sleeve 319 (FIG. 22) and is connected to the core 302.

Figures 23, 24, 25, 26:
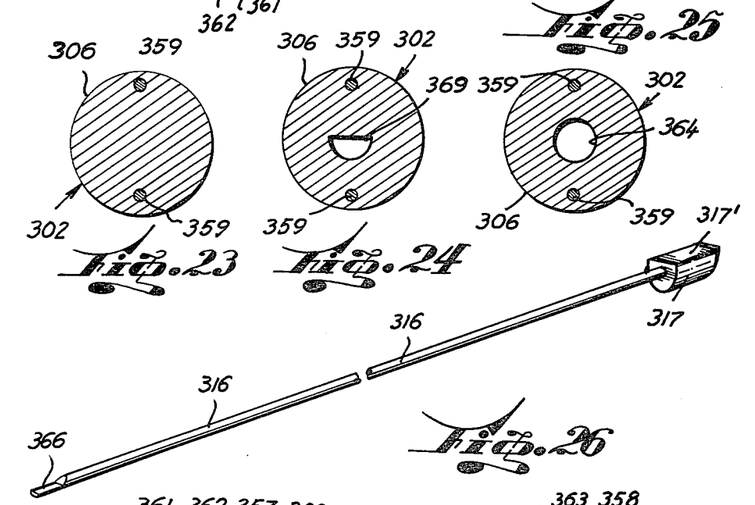
FIG. 23 is a cross-section through the front portion of the electrode tip of the electrode member, shown in FIG. 22.
FIG. 24 is a cross-section through an intermediate portion of the electrode tip of the electrode member, shown in FIG. 22.
FIG. 25 is a cross-section through the rear portion of the electrode tip of the electrode member, shown in FIG. 22.
FIG. 26 is a perspective view of a stylet to be inserted through the rear end portion into the tip of the electrode member.

Referring now to FIG. 26, the stylet 316 is there shown, having an operating knob 317 which includes a flattened surface 317'. The stylet is simply a cylindrical rod having a front end with a flattened portion 366, which performs the same role as the triangular cross-sectional portion 16, shown and described in connection with FIG. 3. To this end the rear portion of the core 302 has a blind bore, which at the beginning is of circular cross-section and identified by reference numeral 364 (FIG. 25) and in the intermediate portion of the core 302 said circular cross-sectional preforation 364 merges into a semi-circular cross-sectional perforation 369 (FIG. 24). The front end portion, as shown in FIG. 23 is solid. Thus, the flattened front end portion 366 of the stylet 316 may be inserted into the semi-circular cross-sectional portion 369 and thereby couple both members to facilitate the insertion and forward movement of the assembly, through the guide member 322. During this insertion, obviously the prongs 357, 358 are in collapsed position. As the electrode is moved forward within the guide member 322, the surgeon or physician will be perfectly capable of determining when the front face 303 reaches the tapered mouth 351, due to the resistance which will be perceived against the forward movement of the electrode member, causing a slight expansion of the wall member 351' (see also FIG. 16). Also a certain resistance to the further forward movement is provided by the myocardium itself, since the cross-section of core 302 is larger than the cross-section of the perforation previously provided in the heart muscle by the end 326 of needle 325.

The fact that the pointed ends 357' (FIG. 27) of the front prongs 357 project slightly out of their recesses 361 beyond the periphery 306, is of no hindrance since these pointed ends 357' are quite resilient. As soon as the resistance to the forward movement of the electrode member decreases, the surgeon realizes that the core 302 has moved beyond the tapered mouth 351, as shown in FIG. 17 and which corresponds in the method of anchoring the electrode member to FIG. 7. At this instant, on the one hand the surgeon can withdraw the guide member 322 from the patient's body in the direction indicated by arrow 41 (FIG. 7), and on the other hand he can now rotate the stylet through approximately 180° to anchor the prongs 357 and 358 in the heart or other organ. In order to facilitate the anchoring, the pointed ends 357', as soon as they have left the tapered mouth 351, penetrate into the mass of the muscle of the organ, so that upon carrying out the rotation, a good penetration of the prongs 357 and 358, which gradually open as they penetrate the muscle, is achieved. The stops 362, 363 will ensure that the prongs 357, 358 will not rotate beyond the predetermined limit. The flattened surface 317' helps the surgeon to know how much he has to rotate the stylet 316, in order to anchor the anchoring prongs correctly.

Conveniently, the sleeve 319 may be coloured or otherwise marked over its rear portion in the zone where the forward movement of the electrode member should be stopped and which would correspond to the portion, which should not enter the rear face 324 of the handle 353. Thus, such a marked portion is a safety guide for the surgeon.

Once the electrode tip has been properly anchored, the stylet 316 is withdrawn and since the guide member 322 has been previously withdrawn, the anchoring of the electrode member has become completed.

The electrical conductor 321 can now be connected to the pacemaker (not shown).

In cases of extreme emergency, one may wish to avoid loss of time by having to entirely withdraw the guide member 322 from the insulating sleeve portion projecting out of the patient's body. Thus axial dismounting of the guide member from the sleeve 319 becomes unnecessary. This allows the conductor 321 to be connected to the pacemaker at an earlier stage, namely once the core has been anchored in the organ. In this event, a guide member of the type of guide member 322 may be provided, but which is either of the disposable type or may be of a split type, in order to open it up along the sleeve portion 319 projecting out of the patient's body.

Obviously, if the electrode member has to be removed from the organ, the steps just described have to be followed in reverse order, but the removal can be carried out without using the guide member 322, provided that the electrode member 302 is constantly rotated by the stylet 316, in the direction to keep the prongs 357, 358 in collapsed position.

The concept of providing a split guide member is obviously not limited to the fourth embodiment.

From the foregoing it is apparent that the present invention likewise relates to a method for implanting from outside of the patient's body a flexible electrode device in an internal organ, such as the heart, without requiring thoracotomy or the like procedure and without lacerating the organ, as would be the case with a rigid electrical conductor member when gaining previous access to the internal organ to be stimulated by electric pulses. The steps of the method involved have been described in most detail in connection with FIGS. 4 to 8 and it will be obvious to those skilled in the art, that these steps can be followed also with the second to fourth embodiments hereinabove described.

It will be understood, that improvements may be introduced in the embodiments described by way of example and modifications may be made in the construction and materials employed, without departing from the scope of the invention.

I claim:

1. A percutaneous implantable electrode device for the transitory or permanent stimulation of the heart or other organs, comprising a core having a front portion and a rear portion, at least one resilient anchoring member, having a first pointed free end and a second end which is linked to said core and which has a substantially complementary housing for said anchoring member, said first pointed free end of said anchoring member having a tendency to project out of its housing, said anchoring member being capable of adopting an inoperative position in which it is substantially housed in said substantially complementary housing, and an operative position in which said anchoring member projects out of said housing with an orientation defining as a maximum an approximately right angle with regard to the axis of the core taking as a reference the rear portion of the core, an electrical conductor connected to at least one of said core and anchoring member, said conductor being arranged in an insulated sheath connected to the rear portion of the core and a hollow substantially rigid tubular guide member having a front end portion defining a perforating mouth and which is slideably mounted on said core and projects beyond the rear portion of said core, said perforating mouth is controlled by depth control means.

2. The electrode device of claim 1, wherein said periphery has a complementary recess to said anchoring member, said first pointed free end of said anchoring member having a tendency to project out of said recess, said anchoring member being capable of adopting an inoperative position in which it is substantially totally housed in said complementary recess and an operative position in which said anchoring member projects out of said recess.

3. The electrode device as claimed in claim 2, wherein said complementary recesses are helically shaped, one of which being arranged nearer said front face of said core than the other and each anchoring member being wound into its pertinent recess with its second end connected to the pertinent recess at the end portion which is nearer said front face of said core.

4. The electrode device of claim 2, wherein each complementary recess is coaxial with the longitudinal axis of said core and each anchoring member is housable in said recess with its second end portion connected to said recess at the portion nearer said front end of said core.

5. The electrode device as claimed in claim 4, wherein said core is hollow and said recesses pass therethrough, said second end of each anchoring member defining a cam arranged in the hollow core on a pertinent torsion axis and an actuating substantially rigid, stylet slideably insertable into said core and capable of entering in caming relationship with said cams to force said anchoring members towards the inside of their pertinent slots.

6. The electrode device of claim 1, wherein said core supports two anchoring members, the pointed free ends of which are substantially diametrically opposite.

7. The electrode device of claim 1, wherein the electrical conductor is tension resistant and connected to one end of said core.

8. The electrode device of claim 1, wherein said hollow rigid tubular guide member is integral with a needle-like tubular member of smaller diameter than said guide member, said needle-like member forming said depth control means, said needle-like tubular member having a front portion defining a perforating end which is located ahead of the perforating mouth of said hollow guide member.

9. The electrode device of claim 1, wherein said core has a blind bore which opens into said rear end and through which an operating stylet is insertable to define a drivable connection between both.

10. A percutaneous insertable electrode device for the transitory or permanent stimulation of the heart or other organs, comprising a substantially rigid tubular guide member provided having a front end forming a first diameter, a needle-like tubular member having a second diameter smaller than said first diameter (and being sufficiently small to allow perforating the endocardium of the heart without creating harm upon withdrawing it), said needle-like tubular member defining a forward end which projects beyond said front end of the tubular guide member by a distance which is approximately equal to half of the mean average thickness of the myocardium of the heart muscle, a core removably housable in said tubular member, said core including projectable and retractable anchoring means and insulated electricity conductor means connected to said core.

11. A percutaneous insertable electrode device for the transitory or permanent stimulation of the heart or other organs, comprising a substantially rigid tubular guide member having a front end, a needle member having a forward end portion, said needle member being longer than said guide member and having an overall cross-section smaller than the internal cross-section of said tubular guide member, said needle member being slideable through said guide member, said needle member including an enlarged sealing portion near said forward end portion adapted to enter in sealing contact with the inside of said front end, an electrode tip including a core pivotally supporting at least one U-shaped anchoring needle formed by a curved front prong, a curved rear prong and a connecting base portion, said connecting base portion being journalled in said core, recessed portions in said core for housing said prongs therein, said core with the prongs housed in their recesses having an overall cross-section smaller than the internal cross-section of said tubular guide member, said prongs being projectable out of said core upon rotating said electrode tips in one direction and being rotatable into said recessed portion upon rotating said electrode in opposite direction to said first direction, an insulated electricity flexible conductor electrically connected at least to one of said core and anchoring needle capable of passing, together with said tip through said guide member, and a dismountable stylet connectable to said core for moving said core forward as well as for rotating it.

12. The electrode device of claim 11, wherein said guide member has a tapered mouth at its front end.

13. The electrode device of claim 12, wherein said stylet has a rear portion with a handle defining a first mark which enables to determine the rotary position of said tip and said insulated electricity flexible conductor has a second mark defining the position of said tip, when the latter is substantially flush with the tapered mouth of said substantially rigid tubular guide member.

14. The electrode device of claim 11, wherein said core is generally cylindrical and supports two diametrically opposite U-shaped anchoring needles.

15. The electrode device of claim 11, wherein the prongs have each a pointed end and the pointed end of each front prong slightly projects out of the pertinent recess, upon said prongs being housed in their recesses.

16. The electrode device of claim 11, wherein the core defines at the zone of confluence of a prong with its connecting base portion a stop, limiting the emerging path of said U-shaped anchoring needle with regard to its core.

17. The electrode device of claim 1, 10 or 11, wherein said rigid tubular guide member is splitable.

18. A method for implanting form outside of the patient's body an electrode device in an internal organ, such as the heart (without requiring thoracotomy or the like procedure to gain previous access to the internal organ to be stimulated by electric pulses), comprising the steps of perforating the patient's skin with a tubular hollow, substantially rigid guide member including at its forward end a forwardly projecting perforating needle, moving said guide member forward towards the organ where the electrode is to be implanted, partially penetrating in said organ from outside with said needle and the forward end of said guide member, detecting the depth of penetration through said needle, passing through said guide member, an electrode tip having projectable and retractable anchoring means at least in the front portion of said tip, the rear portion of which is connected to a flexible insulated electricity conductor, moving said electrode tip forward until said front portion of said tip is substantially flush with the forward end of said guide member, withdrawing the guide member along said electrode tip and insulated electricity conductor out of the patient's body at the same time as the projectable anchoring means are anchored in the internal organ.

19. The method of claim 18, wherein a drug is injected through said needle into the patient's body while advancing toward said internal organ.

20. The method of claim 18, wherein a removable, substantially rigid stylet is connected to the rear portion of said tip, said stylet with said tip is rotated after the guide member has been withdrawn therefrom, in order to anchor the projectable anchoring means in said organ.

21. A percutaneous insertable electrode device for the temporary or permanent stimulation of the heart or other organs, including a substantially rigid tubular guide member shaped to penetrate body tissue, a core removably housable in the tubular member and including projectable and retractable anchoring means and an insulated electrical conductor connected to the anchoring means, a needle-like tubular member having a diameter sufficiently small to allow perforation of the endocardium after having perforated the epicardium and myocardium of the heart without causing damage upon withdrawal, the needle-like tubular member projecting from the front end of the tubular guide member by a distance which is approximately equal to half of the mean average thickness of the myocardium of the heart muscle.

22. The electrode device of claim 21, wherein the needle-like member is fixed to the outside of the tubular guide member and the latter is provided with annular perforating means whereby to penetrate the body tissue.

23. The electrode device of claim 21, wherein the needle-like member extends through the centre of the guide member which is shaped to enter the perforation made by the needle-like member.

* * * * *